US010332723B1

(12) United States Patent
Ibrahim et al.

(10) Patent No.: US 10,332,723 B1
(45) Date of Patent: Jun. 25, 2019

(54) ION FOCUSING DEVICE

(71) Applicant: Battelle Memorial Institute, Richland, WA (US)

(72) Inventors: Yehia M. Ibrahim, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/849,417

(22) Filed: Dec. 20, 2017

(51) Int. Cl.
*H01J 37/08* (2006.01)
*H01J 37/05* (2006.01)
*H01J 49/00* (2006.01)
*H01J 37/317* (2006.01)
*H01J 37/21* (2006.01)
*H01J 49/06* (2006.01)

(52) U.S. Cl.
CPC .......... *H01J 37/3171* (2013.01); *H01J 37/05* (2013.01); *H01J 37/08* (2013.01); *H01J 37/21* (2013.01); *H01J 49/065* (2013.01); *H01J 2237/049* (2013.01); *H01J 2237/30472* (2013.01)

(58) Field of Classification Search
CPC ........ H01J 37/3171; H01J 37/05; H01J 37/08; H01J 37/21; H01J 49/065; H01J 2237/049; H01J 2237/30472
USPC ........................................ 250/281, 282, 283
See application file for complete search history.

(56) References Cited

U.S. PATENT DOCUMENTS

| | | | |
|---|---|---|---|
| 5,572,035 A | 11/1996 | Franzen | |
| 6,107,328 A | 8/2000 | Parsons | |
| 6,960,760 B2 | 11/2005 | Bateman et al. | |
| 7,365,317 B2 | 4/2008 | Whitehouse et al. | |
| 7,391,021 B2 | 7/2008 | Stoermer et al. | |
| 7,786,435 B2 | 8/2010 | Whitehouse et al. | |

(Continued)

FOREIGN PATENT DOCUMENTS

EP   1 566 828 A2   8/2005
EP   1 825 495 B1   11/2011
(Continued)

OTHER PUBLICATIONS

Garimella et al., "Simulation of Electric Potentials and Ion Motion in Planar Electrode Structures for Lossless Ion Manipulations (SLIM)," *J. Am. Soc. Mass Spectrom.* 25(11):1890-1896 (Nov. 2014).

(Continued)

*Primary Examiner* — Nicole M Ippolito
(74) *Attorney, Agent, or Firm* — Klarquist Sparkman, LLP

(57) ABSTRACT

Apparatus include a plurality of electrode arrangements spaced apart from each other opposite an ion propagation axis and defining an ion transfer channel that extends along the ion propagation axis that tapers between an input end that is situated to receive ions and an output end that is situated to couple the received ions to an input end of an ion guide. Methods include positioning a plurality of electrode arrangements at oblique angles opposite an ion propagation axis so as to form a ion transfer channel that tapers between an input end and an output end, and coupling the output end of the ion transfer channel to an input end of an ion optical element so as to direct ions in the ion transfer channel into the ion optical element. Related systems are also disclosed.

20 Claims, 10 Drawing Sheets

(56) References Cited

U.S. PATENT DOCUMENTS

| | | | |
|---|---|---|---|
| 7,838,826 | B1 | 11/2010 | Park |
| 7,888,635 | B2 | 2/2011 | Belov et al. |
| 8,049,169 | B2 | 11/2011 | Satake et al. |
| 8,222,597 | B2 | 7/2012 | Kim et al. |
| 8,637,817 | B1 | 1/2014 | Krutchinsky et al. |
| 8,835,839 | B1 | 9/2014 | Anderson et al. |
| 8,969,800 | B1 | 3/2015 | Tolmachev et al. |
| 2004/0026611 | A1 | 2/2004 | Bateman et al. |
| 2007/0138384 | A1 | 6/2007 | Keiser |
| 2009/0173880 | A1 | 7/2009 | Bateman et al. |
| 2009/0206250 | A1 | 8/2009 | Wollnik |
| 2011/0024618 | A1 | 2/2011 | Brown et al. |
| 2011/0049357 | A1 | 3/2011 | Giles |
| 2011/0192969 | A1 | 8/2011 | Verentchikov |
| 2012/0261570 | A1 | 10/2012 | Shvartsburg et al. |
| 2013/0175440 | A1 | 7/2013 | Perelman et al. |
| 2015/0076343 | A1 | 3/2015 | Tomachev et al. |
| 2016/0225598 | A1 | 8/2016 | Ristroph |
| 2016/0322209 | A1* | 11/2016 | Wouters .................. H01J 9/066 |
| 2017/0076931 | A1 | 3/2017 | Ibrahim et al. |

FOREIGN PATENT DOCUMENTS

| | | |
|---|---|---|
| GB | 2499587 | 8/2013 |
| WO | WO 2016/034125 | 3/2016 |
| WO | WO 2018/048494 | 3/2018 |

OTHER PUBLICATIONS

Giles et al., "A method for direct measurement of ion mobilities using a travelling wave ion guide," *International Journal of Mass Spectrometry*, 298(1):10-16 (Dec. 2010).

Giles et al., "Applications of a travelling wave-based radio-frequency-only stacked ring ion guide," *Rapid Commun. Mass Spectrom.*, 18(20):2401-2414 (Oct. 30, 2004).

Giles et al., "Enhancements in travelling wave ion mobility resolution," *Rapid Commun. Mass Spectrom.*, 25(11):1559-1566 (Jun. 15, 2011).

Glaskin et al., "Ion Trapping for Ion Mobility Spectrometry Measurements in a Cyclical Drift Tube," *Anal. Chem.*, 85(15):7003-7008 (Jul. 2013).

Hamid et al., "Characterization of Traveling Wave Ion Mobility Separations in Structures for Lossless Ion Manipulations," *Anal. Chem.*, 87:11301-11308 (Oct. 28, 2015).

Ibrahim et al., "Development of a new ion mobility (quadrupole) time-of-flight mass spectrometer," *International Journal of Mass Spectrometry*, 377:655-662 (Feb. 1, 2015).

International Search Report and Written Opinion for related International Application No. PCT/US2014/011291, dated Jun. 6, 2014.

International Search Report and Written Opinion for related International Application No. PCT/US2017/039770, dated Dec. 15, 2017.

Merenbloom et al., "Effects of Select Anions from the Hofmeister Series on the Gas-Phase Conformations of Protein Ions Measured with Traveling-Wave Ion Mobility Spectrometry/Mass Spectrometry," *J. Am. Soc. Mass Spectrom.* 22:1978-1990 (Nov. 22, 2011).

PCT Recordation of Search History for International Application No. PCT/US14/11291, International Filing Date Jan. 13, 2014, Date during which the search was conducted May 15 2014, Date of Completion of Recordation of Search History Form dated May 22, 2014.

Pringle et al., "An investigation of the mobility separation of some peptide and protein ions using a new hybrid quadrupole/travelling wave IMS/oa-ToF instrument," *International Journal of Mass Spectrometry*, 261(1):1-12 (Mar. 1, 2007).

Shvartsburg et al., "Fundamentals of Traveling Wave Ion Mobility Spectrometry," *Anal. Chem.*, 80(24):9689-9699 (Dec. 15, 2008).

Smith et al., "Deciphering drift time measurements from travelling wave ion mobility spectrometry-mass spectrometry studies," *European Journal of Mass Spectrometry*, 15(2):113-130 (Jan. 2009).

Sobott et al., "A Tandem Mass Spectrometer for Improved Transmission and Analysis of Large Macromolecular Assemblies," *Anal. Chem.*, 74(6):1402-1407 (Apr. 2002).

Tolmachev et al., "Characterization of Ion Dynamics in Structures for Lossless Ion Manipulations," *Anal. Chem.*, 86(18):9162-9168 (Sep. 16, 2014).

Webb et al., "Experimental Evaluation and Optimization of Structures for Lossless Ion Manipulations for Ion Mobility Spectrometry with Time-of-Flight Mass Spectometry," *Anal. Chem.*, 86(18):9169-9176 (Sep. 5, 2014).

Webb et al., "Mobility-Resolved Ion Selection in Uniform Drift Field Ion Mobility Spectrometry/Mass Spectrometry: Dynamic Switching in Structures for Lossless Ion Manipulations," *Anal. Chem.*, 86(19):9632-9637 (Oct. 7, 2014).

Zhong et al., "Characterizing the resolution and accuracy of a second-generation traveling-wave ion mobility separator for biomolecular ions," *The Royal Society of Chemistry*, 136(17):3534-3541 (Mar. 2011).

Zhang et al., "Ion Trapping, Storage, and Ejection in Structures for Lossless Ion Manipulations," *Anal. Chem.*, 87(12):6010-6016 (May 2015).

Ibrahim et al., "New frontiers for mass spectrometry based upon structures for lossless ion manipulations," The Analyst, 142(7):1010-1021 (Mar. 3, 2017).

International Search Report and Written Opinion for related International Application No. PCT/US2018/065380, dated Mar. 29, 2019, 12 pages.

\* cited by examiner

ION FOCUSING DEVICE

ACKNOWLEDGMENT OF GOVERNMENT SUPPORT

This invention was made with government support under DE-AC05-76RL01830 awarded by the United States Department of Energy. The government has certain rights in the invention.

FIELD

The field is ion focusing devices.

BACKGROUND

Ion manipulation has allowed the discovery of new applications related to material synthesis and analysis, and has fostered the creation of increasingly useful tools and instruments related to, for example, mass spectrometry. However, problems associated with directing and transferring ions have remained.

SUMMARY

Methods and apparatus for directing and transferring ions are disclosed.

According to an aspect of the disclosed technology, apparatus include a plurality of electrode arrangements spaced apart from each other opposite an ion propagation axis and defining an ion transfer channel that extends along the ion propagation axis that tapers between an input end that is situated to receive ions and an output end that is situated to couple the received ions to an input end of an ion guide. In some examples, the received ions are coupled at the output end to the input end of the ion guide with an electric field that is matched to the input end of the ion guide. In representative examples, the electrode arrangements are arranged in respective electrode arrangement planes, each extending at a respective oblique angle with respect to the ion propagation axis. In some examples, each of the respective oblique angles is less than or equal 60 degrees and greater than or equal 5 degrees. In further examples, at least one of the electrode arrangements includes a plurality of RF electrodes extending in the direction of the ion propagation axis in the plane of the at least one electrode arrangement so that RF electrodes are situated to direct the ions away from the at least one electrode arrangement, wherein the at least one electrode arrangement includes a plurality of traveling wave electrode sets interspersed between the RF electrodes and extending in the direction of the ion propagation axis in the plane of the at least one electrode arrangement so that the traveling wave electrode sets are situated to direct the ions towards the output end of the ion transfer channel. In some examples, the at least one electrode arrangement is tapered such that there are fewer RF electrodes and traveling wave electrode sets at the output end of the ion transfer channel than at the input end of the ion transfer channel. In further examples, at least one of the electrodes at the input end that is not at the output end is non-rectangular based on an angle defined by the tapering of the at least one electrode arrangement. According to some embodiments, guard electrodes are situated opposite the plurality of RF electrodes and plurality of traveling wave electrode sets of the at least one electrode arrangement so as to direct the ions away from the pair of guard electrodes and into the ion transfer channel between the guard electrodes. In some examples, the guard electrodes comprise an opposing pair of DC electrodes, an opposing pair of RF electrode stacks, or an opposing pair of traveling wave electrode sets. In further examples, each of the traveling wave electrode sets includes a plurality of traveling wave electrodes situated to receive a traveling wave voltage that varies over time so as to direct the ions along toward the output end of the ion transfer channel. In additional examples, the RF electrodes and traveling wave electrodes at the output end of the ion transfer channel are matched in size, shape, RF voltage signal, or traveling wave voltage signal of respective electrodes at the input end of the ion guide. According to some embodiments, the ions directed by the apparatus have the same or different polarities.

According to another aspect of the disclosed technology, methods include positioning a plurality of electrode arrangements at oblique angles opposite an ion propagation axis so as to form a ion transfer channel that tapers between an input end and an output end, and coupling the output end of the ion transfer channel to an input end of an ion optical element so as to direct ions in the ion transfer channel into the ion optical element. In some embodiments, the coupling includes matching an electric field provided by the ion transfer channel at the output end with an electric field provided by the ion optical element. In further embodiments, ions are generated with an ion source and the ions are collected in the ion transfer channel. In additional examples, methods include directing the ions in the ion transfer channel to the output end with an electric field provided by the plurality of electrode arrangements. In further examples, methods include directing the ions at the output end into the input end of the ion optical element with the matching electric field. In some examples, at least one of the electrode arrangements includes a plurality of RF electrodes and traveling wave electrode sets arranged in a plane and the arrangement is tapered in the plane such that there are fewer RF electrodes and traveling wave electrode sets at the output end of the ion transfer channel than at the input end of the ion transfer channel. In further examples, the electrode arrangements include guard electrodes situated opposite a plurality of RF electrodes and traveling wave electrode sets so as to direct the ions away from the pair of guard electrodes and into the ion transfer channel between the guard electrodes, and wherein the guard electrodes include an opposing pair of DC electrodes, an opposing pair of RF electrode stacks, or an opposing pair of traveling wave electrode sets.

According to a further aspect of the disclosed technology, systems include at least one processor, and one or more computer-readable storage media including stored instructions that, responsive to execution by the at least one processor, cause the system to control electric potentials of RF electrodes and traveling wave electrodes in a plurality of electrode arrangements spaced apart from each other opposite an ion propagation axis and defining an ion transfer channel that extends along the ion propagation axis that tapers between an input end that is situated to receive ions and an output end that is situated to couple the received ions to an input end of an ion guide so that the ions are directed into the ion guide.

The foregoing and other objects, features, and advantages of the disclosed technology will become more apparent from the following detailed description, which proceeds with reference to the accompanying figures.

DETAILED DESCRIPTION

Figure 1A:
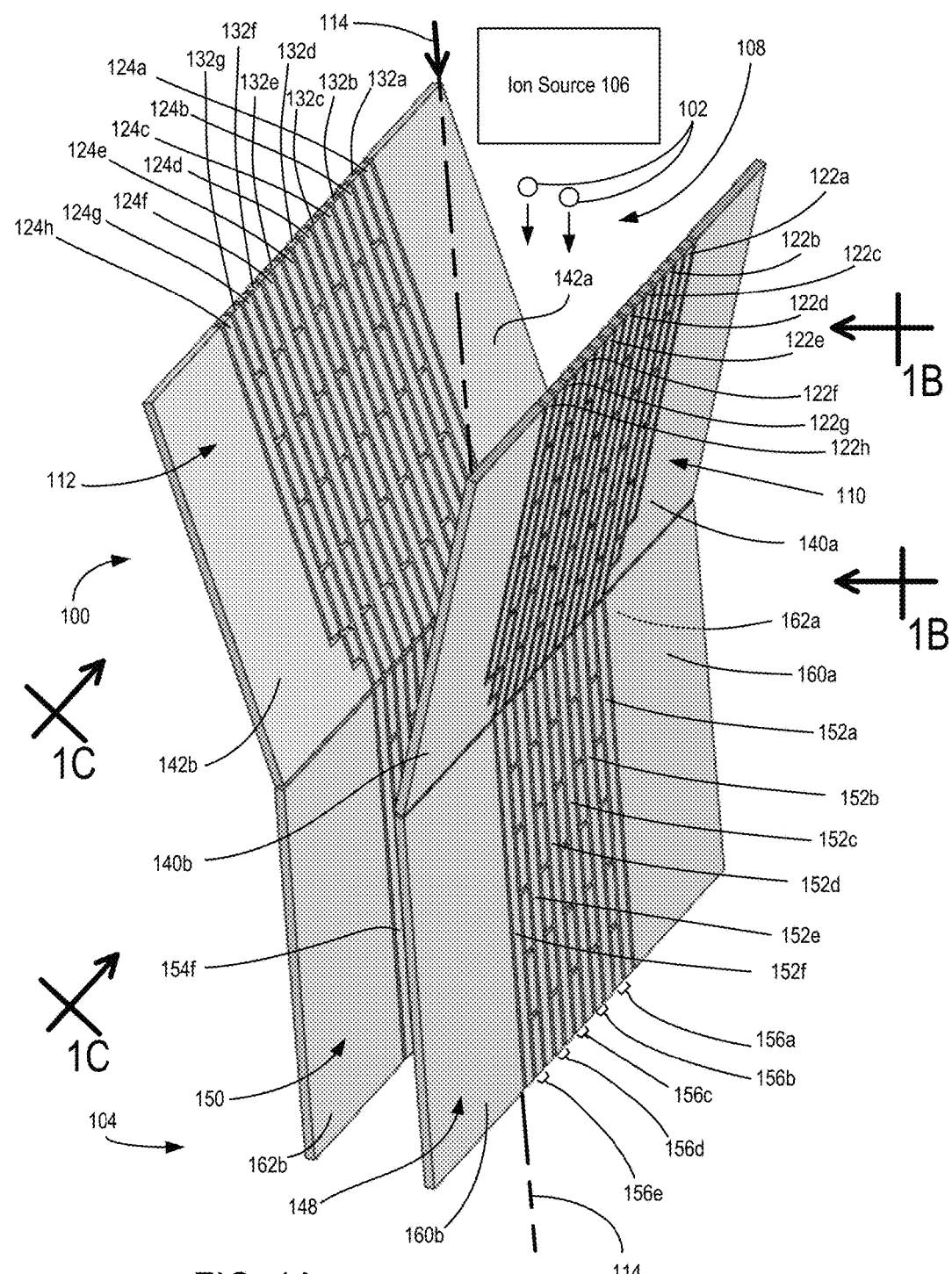
FIG. 1A is a top view of an example ion focusing device.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus are referred to as "lowest," "best," "minimum," or the like. It will be appreciated that such descriptions are intended to indicate that a selection among many used functional alternatives can be made, and such selections need not be better, smaller, or otherwise preferable to other selections.

Some examples are described in relation to one more longitudinal and lateral directions generalized to correspond to ion movement or confinement. Directions typically apply to ion movement, trapping, and confinement and are provided by electric fields produced by one or more electrodes that are arranged to define one or more volumes or channels of various shapes, sizes, and configurations. A direction can correspond to a single path, multiple paths, bi-directional movement, inward movement, outward movement, or a range of movements. Actual ion movement paths vary and can depend on the various characteristics of the electrode arrangements and electric fields produced by the corresponding electrodes and the positional, polarity, kinetic, or other characteristics of the ions received in a confinement volume. Directions referred to herein are generalized and actual specific particle movements typically correspond to electric fields produced and the electrical mobilities of the ions propagating in relation to the electric fields.

The disclosed technology is directed to devices, apparatus, and methods of manipulating ions, including the use of electric fields to create field-defined channels to direct ions with minimal or no losses. In some examples, ion confining fields are provided by unbiased radio frequency (RF) electric fields. In additional examples, ion confining fields provided by unbiased RF fields and traveling wave electric fields. In representative examples, ions of opposite polarity are moved, trapped, or manipulated using RF electric fields or RF and traveling wave electric fields. RF electric fields are typically applied so that RF fields generated by adjacent RF electrodes are out of phase, typically by approximately 180°, to form an alternating RF field arrangement that inhibits the ions from approaching the electrodes and that provides confinement. Confinement can be provided over a range of pressures (e.g., less than approximately 0.001 torr to approximately 1000 torr), and over a useful, broad, and adjustable mass to charge (m/z) range associated with the ions. In some examples ions are manipulated for analysis through mass spectrometry or with a mass spectrometer, and where pressures of less than approximately 0.1 torr to approximately 50 torr can be used to readily manipulate ions over a useful m/z range, e.g., m/z 20 to greater than approximately 5,000. In some examples, ion confinement volumes includes gases or reactants. Arrangements of RE electrodes and traveling wave electrodes receive corresponding potentials that allow creation of ion channels in the volume or gap between the electrode arrangements with a broad acceptance aperture so that lossless or substantially lossless coupling of ions to a narrower aperture can be achieved. Collection and coupling can include losses of less than 0.1%, 1%, or 5% of ions injected into a downstream ion optical component (such as an ion guide).

Traveling waves are typically created by dynamically applying DC potentials to a plurality of electrodes arranged in one or more sequences. Traveling wave electrode sets can be formed by one or more sequences of traveling wave electrodes situated in series. As the DC potentials are varied between adjacent electrodes of a traveling wave electrode sequence, a traveling wave can be formed with a speed based on the time dependent variation of the DC potentials. Varying traveling wave characteristics can affect and manipulate various movements of ions having different ion mobilities, including producing ion confinement, lossless transport, and ion separation. In representative examples, traveling waves are used to losslessly direct ions along an ion channel, from a larger aperture to a narrower aperture. One traveling wave characteristic is the traveling wave speed, with ions that have higher mobility moving or surfing with the traveling wave and ions that have lower mobility rolling over and lagging behind the traveling wave to allow ion separation. Traveling wave speed can be varied so as to produce movement and separation, and to gate groups of ions that are directed into subsequent ion manipulation components. Another traveling wave characteristic is traveling wave amplitude, which can transport ions with lower ion mobilities with a corresponding increase in traveling wave amplitude. Traveling wave amplitudes are typically selected based on ion mobility characteristics and the desired ion manipulation to be in the range of greater than 0 V up to 30 V, 50 V, 80 V, 100 V, or greater. Traveling wave speeds are typically selected based on ion mobility characteristics and the desired ion manipulation to be in the range of less than 5 m/s, 20 m/s 50 m/s, 100 m/s, 200 m/s, or 500 m/s. Traveling wave frequencies are typically selected between 10 kHz and 200 kHz.

Figure 1B:
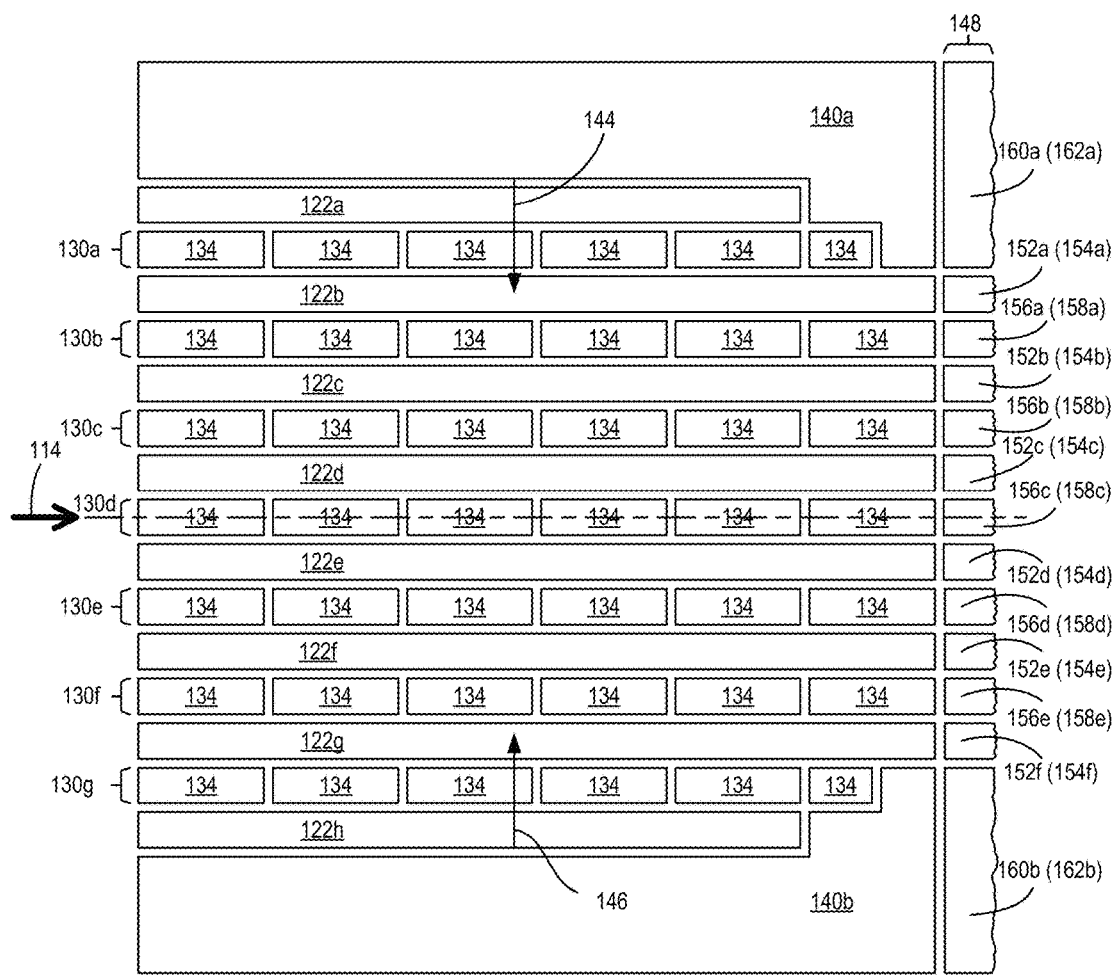
FIG. 1B is a side view of the example ion focusing device shown in FIG. 1A.
Figure 1C:
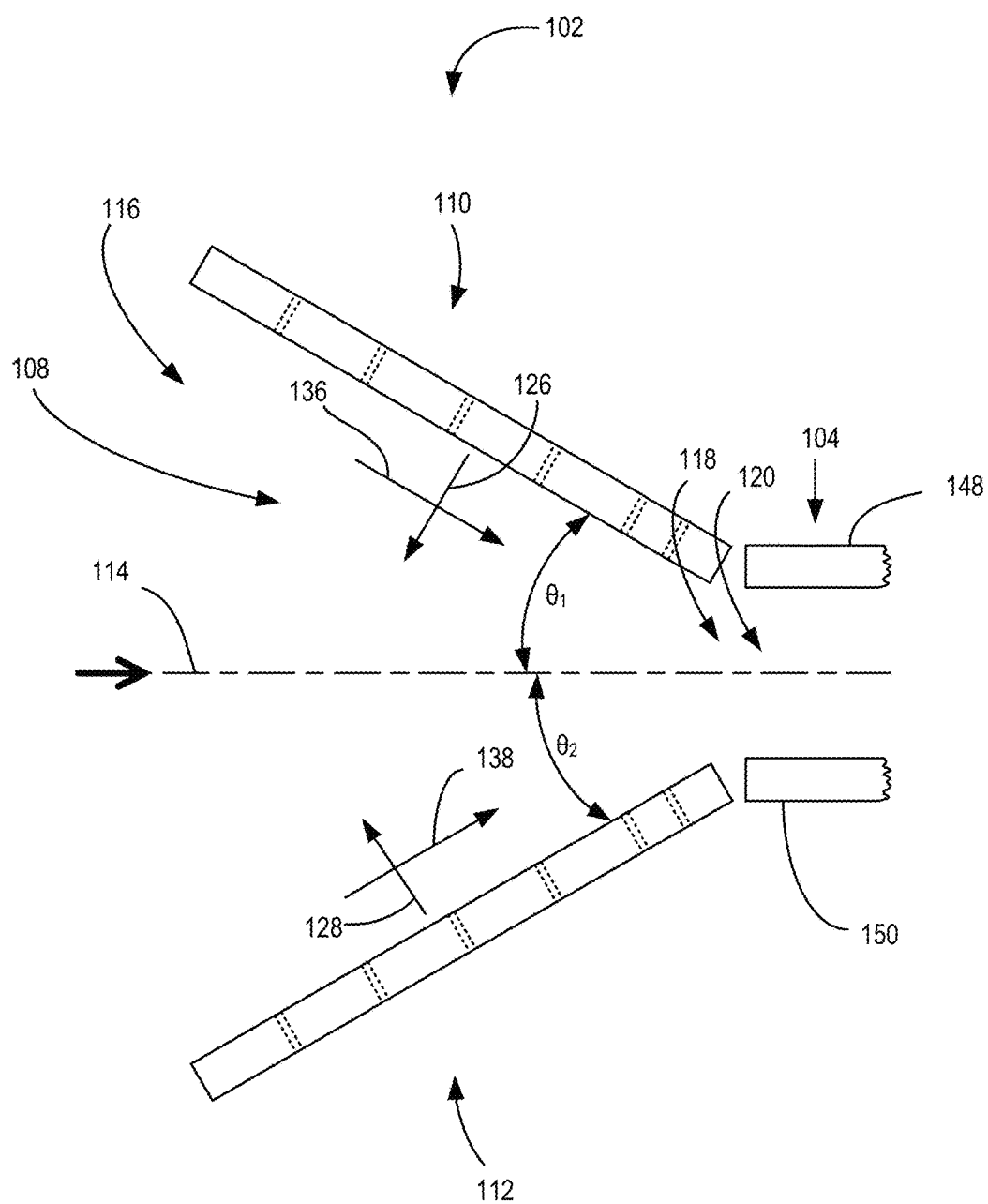
FIG. 1C is a perspective view of the example ion focusing device shown in FIGS. 1A-1B.

FIGS. 1A-1C show an example ion focusing device 100 situated to receive ions 102 having various characteristics (mass, polarity, velocity, etc.) and to direct the ions into an ion optical element, such as an ion guide 104. In representative examples, the ions 102 are collected from an ion source 106 and ion losses are reduced so as to provide efficient ion transfer to the ion guide 104. The ion focusing device 100 collects and transfers the ions 102 to the ion guide 104 with a tapered ion transfer channel 108 that is defined by a pair of electrode arrangements 110, 112 spaced apart from each other opposite an ion propagation axis 114. The tapering of the ion transfer channel 108 provides a large aperture at an input end 116 to efficiently collect the ions 102 having various trajectories, and a smaller aperture at an output end 118 to couple the ions 102 into an input aperture 120 of the ion guide 104. The tapering can define respective oblique angles $\theta_1$, $\theta_2$ (or effective angles if the electrode arrangements are not planar) between the respective electrode arrangements 110, 112 and the ion propagation axis 114. In typical examples, $\theta_1$ is equal to $\theta_2$ though non-equal angles are possible. As shown, angles $\theta_1$, $\theta_2$ are at 30 degrees with respect to the ion propagation axis 114. In further examples, $\theta_1$, $\theta_2$ are at 5 degrees, 15 degrees, 45 degrees, 60 degrees, or other angles. In representative embodiments, an electric field produced by the electrode arrangements 110, 112 at the output end 118 is synchronized or smoothly matched to an electric field produced by the ion guide 104 at the ion guide input aperture 120. In some examples, the ions 102 can have the same polarities or different polarities. Representative examples of the ion focusing device 100 can substantially relieve engineering constraints associated with precise alignment of ion optics, such as between planar ion guides and ion sources, and therefore can substantially reduce the cost of building ion manipulation platforms.

In some examples, the opposing electrode arrangements 110, 112 are planar and include respective pluralities of radio frequency (RF) electrodes 122a-122h, 124a-124h that extend in the direction of the ion propagation axis 114, e.g., along the planes of the respective electrode arrangements 110, 112 from the input end 116 towards the output end 118. Adjacent electrodes of the RF electrodes 122a-122h, 124a-124h are typically driven out of phase with respect to each other (e.g., 122a, 122c driven in-phase and 122b driven out of phase) so that the ions 102 propagating in the ion transfer channel 108 are directed away from the respective electrode arrangement 110, 112, e.g., as shown with arrows 126, 128. The opposing electrode arrangements 110, 112 can also include respective pluralities of sets of traveling wave electrodes 130a-130g, 132a-132g that also extend in the direction of the ion propagation axis 114. Each of the sets of traveling electrodes 130a-130g, 132a-132g includes respective pluralities of traveling wave electrodes 134 that can be driven at time varying DC voltages and synchronized in the respective plurality so that a traveling wave is formed in the direction of the ion propagation axis 114. The traveling wave electric fields can direct the ions 102 along the ion transfer channel 108 from the input end 116 to the output end 118, e.g., as shown with arrows 136, 138. The sets of traveling wave electrodes 130a-130g, 132a-132g are typically alternately interspersed between the RF electrodes 122a-122h, 124a-124h.

In representative embodiments, the opposing electrode arrangements 110, 112 include an electrode tapering in the respective electrode planes. The electrode tapering can reduce the number of electrodes at the output end 118 that are presented to the input aperture 120 of the ion guide 104 as compared to the number of electrodes at the input end 106. For example, the outer RF electrodes 122a, 122h can extend shorter lengths than the inner RF electrodes 122b-122g, or can terminate before the output end 118. Similarly, the outer RF electrodes 124a, 124h can extend reduced lengths or terminate before the output end 118. Interspersed sets of traveling wave electrodes 130a, 130g, 132a, 132g can also extend less than the entire length from the input end 106 to the output end 118. In some examples, the number of traveling wave electrodes 134 in the sets of traveling wave electrodes 130a, 130g, 132a, 132g can be the same as or smaller than the number of traveling wave electrodes 134 in the inner sets of traveling wave electrodes 130b-130f, 132b-132f. Various taper shapes or combinations of shapes can be formed and associated with reduced electrode or electrode set lengths, including one or more of trapezoidal, triangular, inward curving, outward curving, asymmetrical, rectangular, etc.

Opposing guard electrodes 140a, 140b are situated adjacent to, and in the plane of, the electrode arrangement 110, and opposing guard electrodes 142a, 142b are situated adjacent to, and in the plane of, the electrode arrangement 112. The guard electrodes 140a, 140b, 142a, 142b are typically biased with a DC voltage so as to direct the ions 102 away from the guard electrodes 140a, 140b, 142a, 142b so as to be situated between the opposing electrode arrangements 110, 112 in the ion transfer channel 108, e.g., in the directions indicated by arrows 144, 146. The guard electrodes 140a-140b, 142a-142b can be shaped to complement a tapered shape of the respective electrode arrangements 110, 112. In typical examples, the electrode arrangements 110, 112 and the guard electrodes 140a, 140b can be formed on printed circuit board, using 3D printing, or other substrates suitable for ion manipulation. Electrode size and spacing can be varied based on electric field requirements for different ions, coupling efficiencies, and input parameters for ion optical elements (e.g., particle energy, density, timing, etc.). Electrode spacing typically provides a minimum non-conductive area between electrodes to reduce the probability of electrical shorts or interference. In typical examples, minimum spacing and electrode size is on the order of millimeters, including as low as about 0.5 mm, though other dimensions are possible. Square and rectangular shapes can simplify construction and can define device features or boundaries (e.g., sides, apertures, etc.), some of which can be used to register against other ion guides or devices.

The input aperture 120 of the ion guide 104 or ion optical element is coupled or can be coupled to the output end 118 of the ion focusing device 100. In some embodiments, the ion focusing device 100 can be formed as an integral part of the ion guide 104, and in further embodiments, the ion focusing device 100 can be a separate device that can be coupled to various ion optical elements. In particular embodiments, the oblique angles $\theta_1$, $\theta_2$ between the ion propagation axis 114 and the electrode arrangements 110, 112 can be varied with one or more hinges, translation stages, or other angle varying devices, including with the ion focusing device 100 situated separately or as attached or a part of the ion guide 104. In some examples, the ion guide 104 can include one or more electrode arrangements, such as opposing electrodes arrangements 148, 150, that match one or more characteristics of the respective electrode arrangements 110, 112 so as to smoothly couple the ions 102 from the ion transfer channel 108 to the ion guide 104. In one embodiment, the electrode arrangements 148, 150 include a plurality of RF electrodes 152a-152f, 154a-154f and traveling wave electrode sets 156a-156e, 158a-158e that are shaped and spaced at the input aperture 120 similarly to the RF electrodes 122b-122g, 124b-124g and the traveling wave electrode sets 130b-130f, 132b-132f at the output end 118. The electrodes 154a-154f, 158a-158e are shown parenthetically in FIG. 1B as hidden in the view below the electrodes 152a-152f, 156a-156e. In some examples, the electrode arrangements 148, 150 can respectively contact the electrode arrangements 110, 112 or can respectively continuously extend from the electrode arrangements 110, 112. In representative examples, the electrode arrangements 110, 112 are respectively spaced apart from the electrode arrangements 148, 150.

In some embodiments, an RF voltage signal applied to RF electrodes 122b-122g, 124b-124g of the electrode arrangements 110, 112 can be synchronized or applied similarly to RF electrodes 152a-152f, 154a-154f of the electrode arrangements 148, 150. In further embodiments, a traveling wave voltage signal applied to traveling wave electrode sets 132b-132f, 134b-134f can be synchronized or applied similarly to traveling wave electrode sets 156a-156e, 158a-158e. Representative examples of the ion guide 104 also include DC guard electrodes 160a, 160b, 162a, 162b that are situated to direct the ions 102 received in the ion guide 104 away from lateral sides of the ion guide 104 and between the electrode arrangements 148, 150. In various examples, voltage signals applied to the electrode arrangements 148, 150 or to other electrodes (not shown) of the ion guide 104 adjacent to the electrode arrangements 148, 150 can be the same or different from the voltage signals applied to the electrode arrangements 110, 112 based on selected ion activity or application in the ion guide 104, such as ion filtering, ion separation, ion gating, mass spectrometry, time-of-flight control, ion beam cross-section variation (e.g., circular, non-circular, elliptical, symmetric, asymmetric, etc.) etc.

Figure 2:
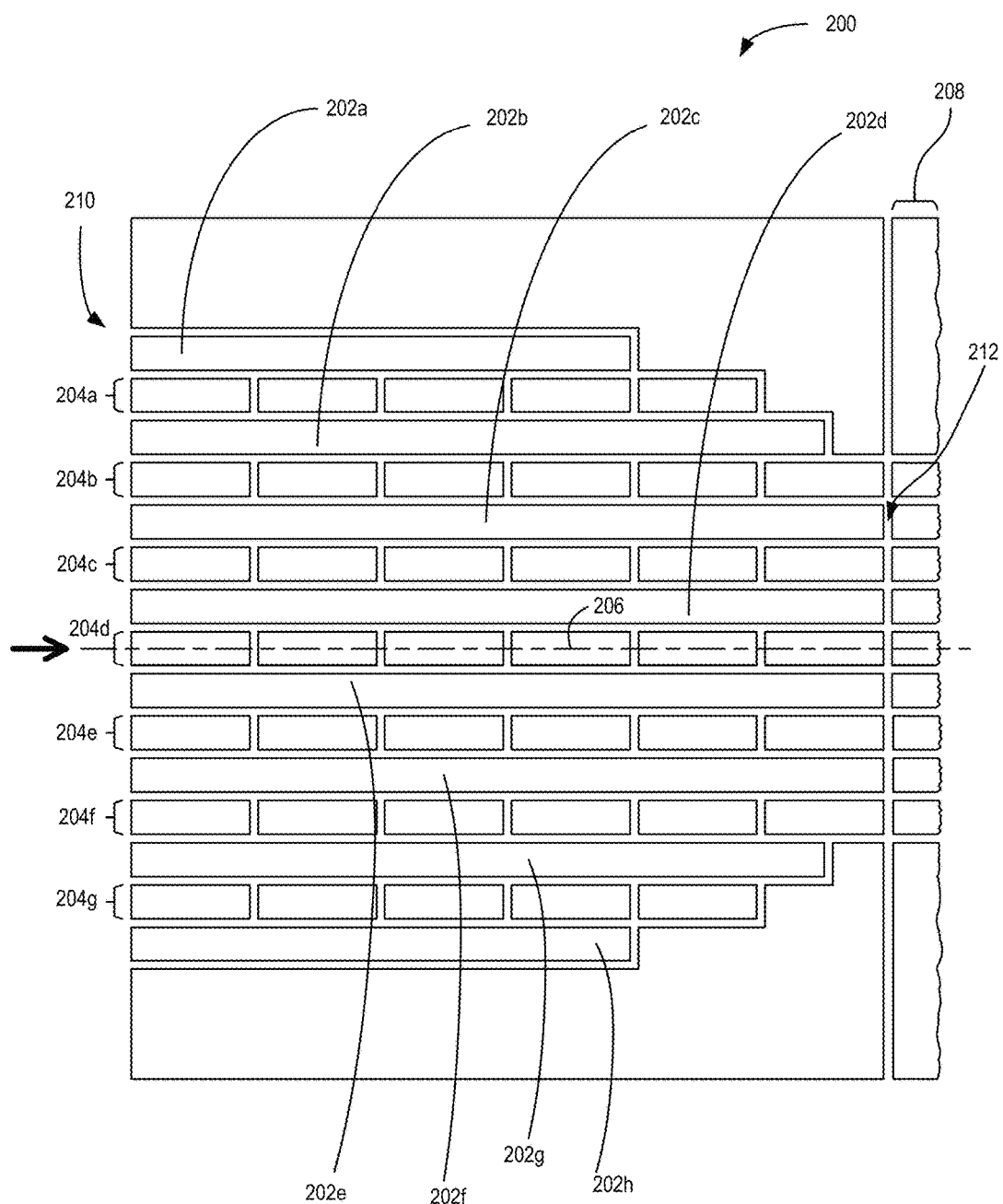
FIG. 2 is a top view of an example ion focusing device.

In FIG. 2, an ion focusing device 200 includes RF electrodes 202a-202h and traveling wave electrode sets 204a-204g that are situated parallel to each other and at an oblique angle (into the plane of FIG. 2) to an ion propagation axis 206. A set of similar electrodes oppositely situated about the ion propagation axis 206 at a similar oblique angle and that assists with directing collected ions to an ion optical element 208 is omitted for clarity. Outer RF electrodes 202a-202b, 202g-202h and traveling wave electrode sets 204a, 204g extend lengths shorter than inner RF electrodes 202c-202f and traveling wave electrode sets 204b-204f so as to define an electrode tapering between an input end 210 and an output end 212 of the ion focusing device 200. Opposing guard electrodes 214, 216 are also situated to direct ions away from the respective guard electrodes 214, 216 so that the ions are kept within the ion focusing device 200.

Figure 3:
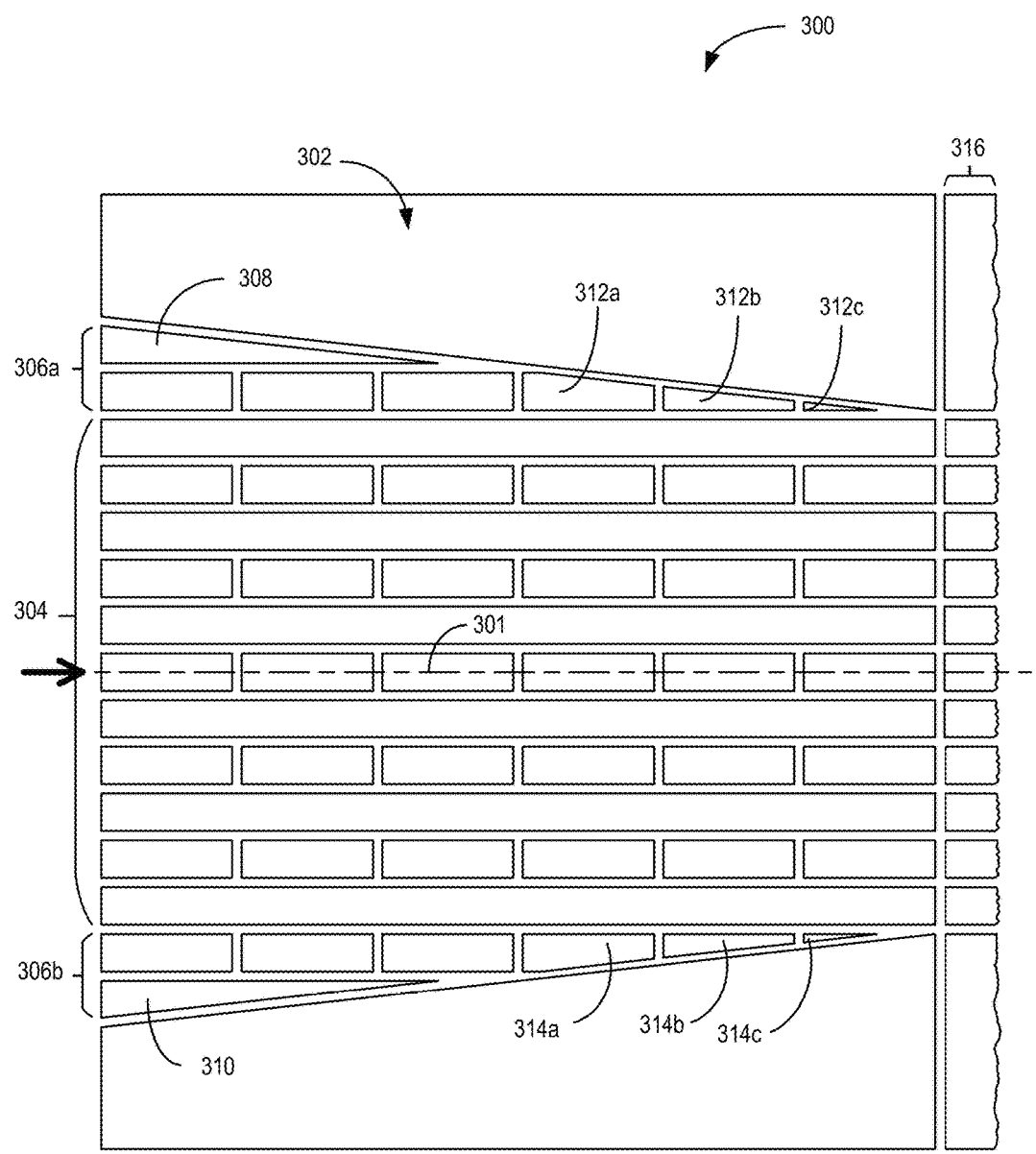
FIG. 3 is a top view of another example ion focusing device.
Figure 4A:
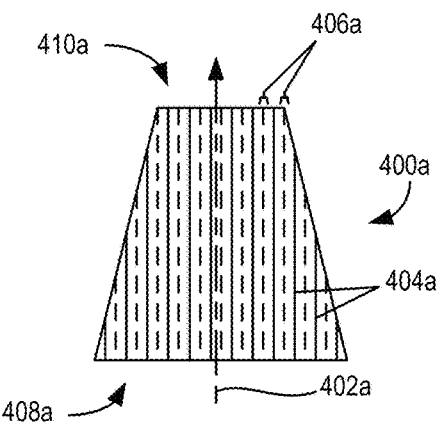
FIGS. 4A-4F are top view schematics of different examples of electrode arrangements.
Figure 4B:
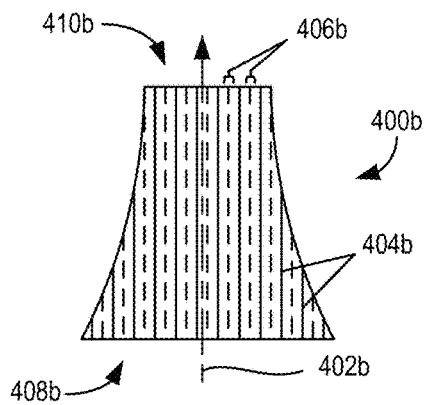
Figure 4C:
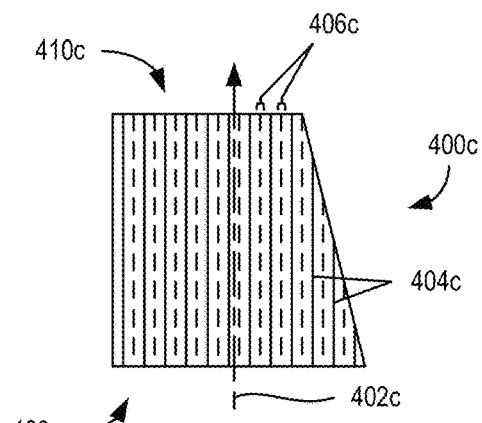
Figure 4D:
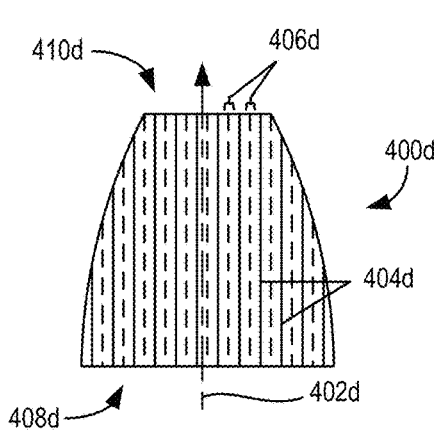
Figure 4E:
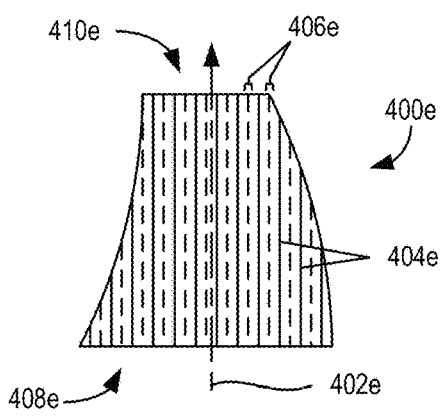
Figure 4F:
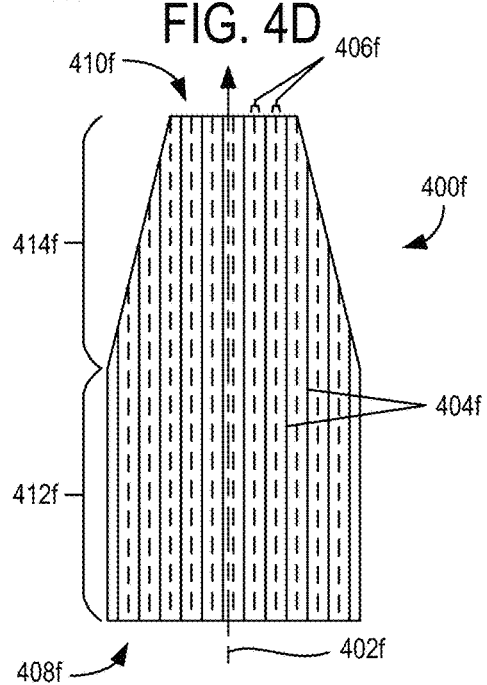

FIG. 3 is another example of an ion focusing device 300 having an ion propagation axis 301 and that includes an electrode arrangement 302 having a set 304 of inner RF electrodes and traveling wave electrode sets. The electrode arrangement 302 further includes opposite, tapered outer electrode sets 306a, 306b including respective non-rectangular RF electrodes 308, 310 and non-rectangular traveling wave electrodes 312a-312c, 314a-314c. The ion focusing device 300 can be situated to collect ions from an ion source and to direct the collected ions to an ion guide 316 situated downstream along the ion propagation axis 301.

FIGS. 4A-4F are different examples of tapered planar electrode arrangements 400a-400f that can be used with one or more other planar electrode arrangements situated at angles in relation to respective ion propagation axes 402a-402f to form respective tapered ion focusing channels. Each of the electrode arrangements 400a-400f can include a plurality of longitudinally extending RF electrodes 404a-404f and traveling wave electrode sets 406a-406f that extend various lengths. The RF electrodes 404a-404f generally maintain ions between the respective electrode arrangements 400a-400f and other electrode arrangements of the tapered ion focusing channels. The traveling wave sets 406a-406f are generally situated to move the ions in the ion focusing channels in the direction of the ion propagation axes 402a-402f. The electrode arrangement 400a is arranged in a trapezoidal configuration extending from a channel input 408a to a channel output 410a that can be coupled with subsequent ion manipulation elements. Sides of the electrode arrangement 400b curve inwardly between a channel input 408b and a channel output 410b. In the electrode arrangement 400c, one side of the electrode arrangement 400c is tapered between a channel input 408c and a channel output 410c, and an opposite side extends parallel to the RF electrodes 404c, the traveling wave electrode sets 406c. The electrode arrangement 400d is similar to the electrode arrangement 400b except that opposite tapered sides curve outward between a channel input 408d and a channel output 410d. The electrode arrangement 400e shows an asymmetric configuration that includes opposite tapered inward-curving and outward-curving sides extending between a channel input 408e and a channel output 410e. Various combinations of electrode arrangement geometries can be formed as well, and electrode arrangement 400f shows one such example with a rectangular electrode arrangement portion 412f extending from a channel input 408f a predetermined length and a trapezoidal electrode arrangement portion 414f extending from an end of the rectangular electrode arrangement portion 412f to a channel output 410f.

Figure 5A:
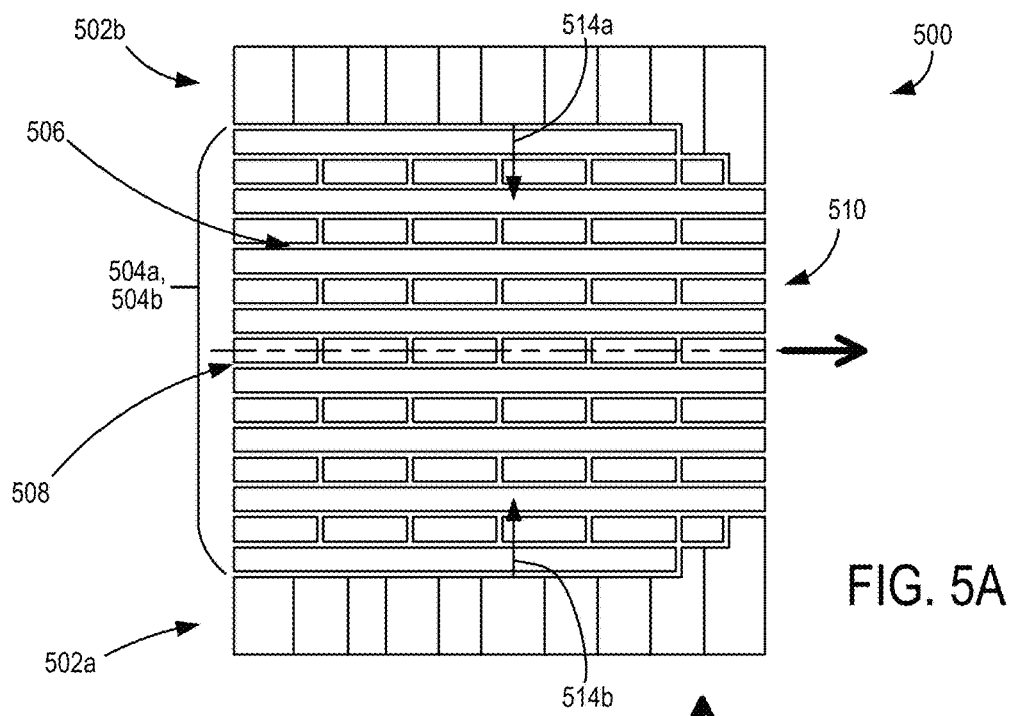
FIGS. 5A-5B are respective top and side views of another example of an ion focusing device.
Figure 5B:
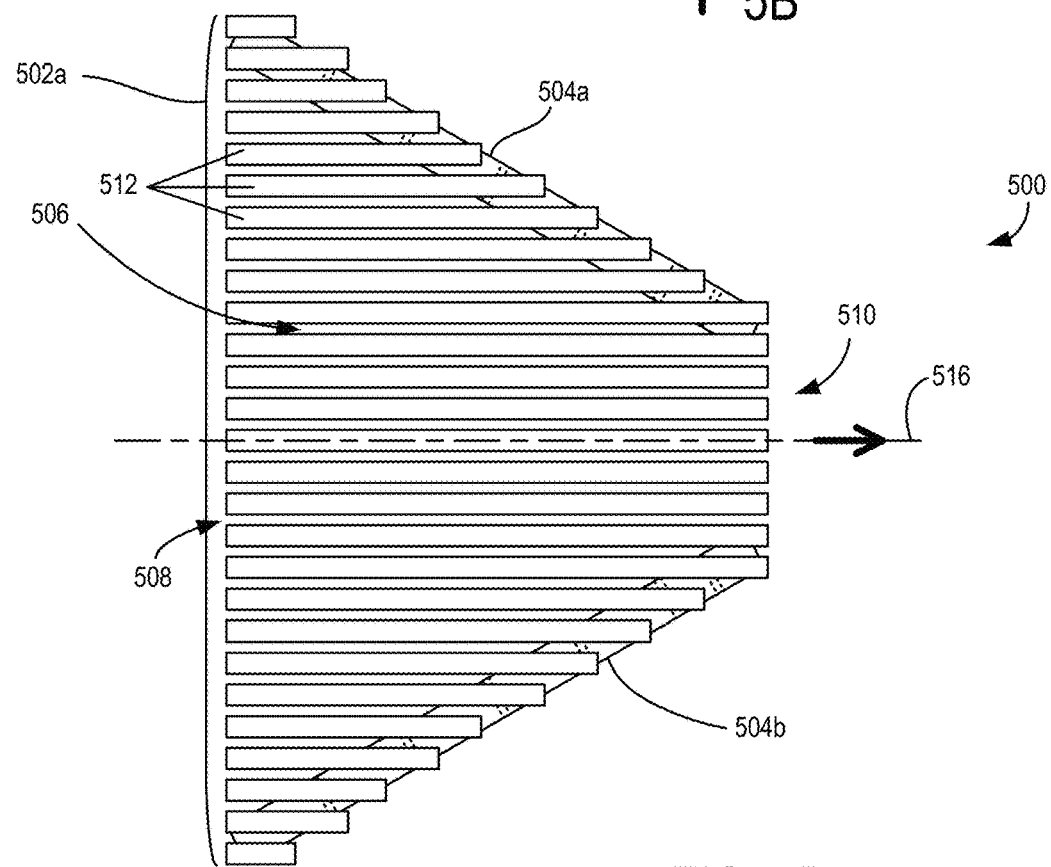

FIGS. 5A-5B depict an example of an ion focusing device 500 that includes guard electrode sets 502a, 502b situated at opposite ends of opposing electrode arrangements 504a, 504b so as to define an ion focusing channel 506 between an input aperture 508 and an output aperture 510. The guard electrodes 502a, 502b include respective pluralities of adjacent RF electrodes 512 forming stacked arrangements that are situated to direct ions into the ion focusing channel 506, e.g., in the direction of arrows 514a, 514b. In typical examples, the alternate RF electrodes are biased out of phase so as to provide the directing of the ions into the interior of the ion focusing channel 506. As shown in FIG. 5B, the RF electrodes 512 of the guard electrode set 502a generally extend parallel to an ion propagation axis 516. In typical examples, the RF electrodes of the guard electrode 502b can also extend parallel to the ion propagation axis 516. Also, as shown in FIG. 5B, the RF electrodes 512 can define an electrode tapering towards the output aperture 510. In some examples, all or additional RF electrodes of the guard electrode sets 502a, 502b can extend equal lengths between the input aperture 508 and the output aperture 510. In additional examples, the RF electrodes 512 of one or both of the guard electrode sets 502a, 502b are not parallel to each other. For example, one or more of the RF electrodes 512 can be parallel to planes defined by one of the opposing electrode arrangements 504a, 504b or at other angles.

Figure 6:
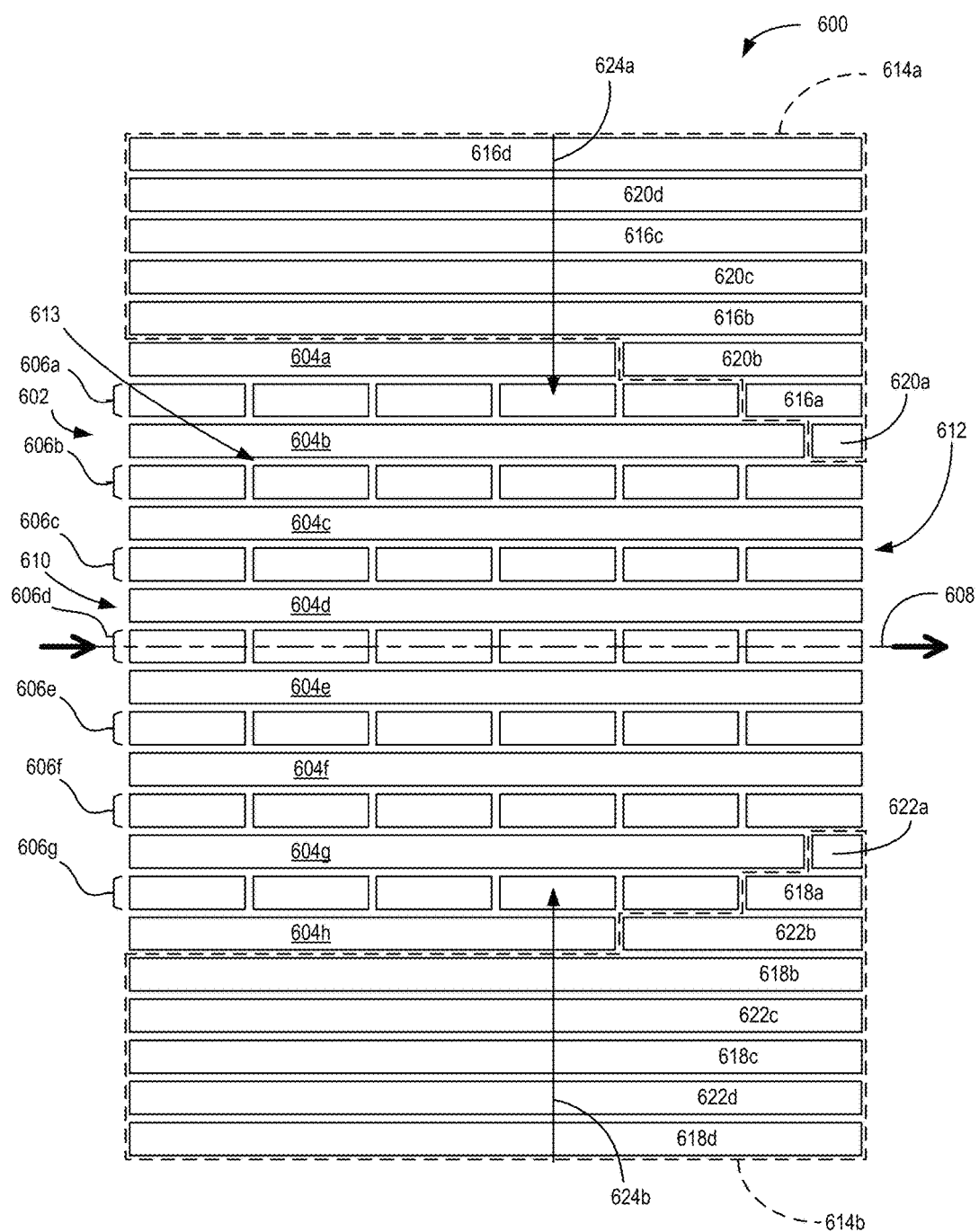
FIG. 6 is a top view of another example ion focusing device.

In FIG. 6, an ion focusing device 600 is shown that includes a planar electrode arrangement 602 that includes RF electrodes 604a-604h and longitudinal traveling wave sets 606a-606g arranged similar to the arrangement RF electrodes 202a-202h and traveling wave electrode sets 204a-204g shown in FIG. 2. The ion focusing device 600 is generally situated to direct ions along an ion propagation axis 608 between an input aperture 610 and an output aperture 612. The ion propagation axis 608 is generally arranged at an oblique angle (into the plane of FIG. 6) to the planar electrode arrangement 602, and a similar opposing electrode arrangement (below the electrode arrangement 602 and not shown) can also be arranged at an angle with respect to the ion propagation axis so as to define a tapering of an ion propagation channel 613 defined between the electrode arrangement 602 and the opposing electrode arrangement between the input aperture 610 and output aperture 612. Opposing guard electrodes 614a, 614b are also situated opposite the electrode arrangement 602 and include alternating RF electrodes 616a-616d, 618a-618d and interspersed traveling wave electrodes 620a-620d, 622a-622d. The RF electrodes 616a-616d, 618-618d direct ions between the planar electrode arrangement 602 and the opposing electrode arrangement (e.g., into the plane of FIG. 6) so that the ions are kept in the ion propagation channel 613. The traveling wave electrodes 620a-620d, 622a-622d are situated to direct the ions towards the ion propagation axis 608, e.g., in the direction of arrows 624a, 624b, so that ions can also be directed according to a tapering of the electrodes in the plane of the planar electrode arrangement 602 towards the output aperture 612.

Figure 7:
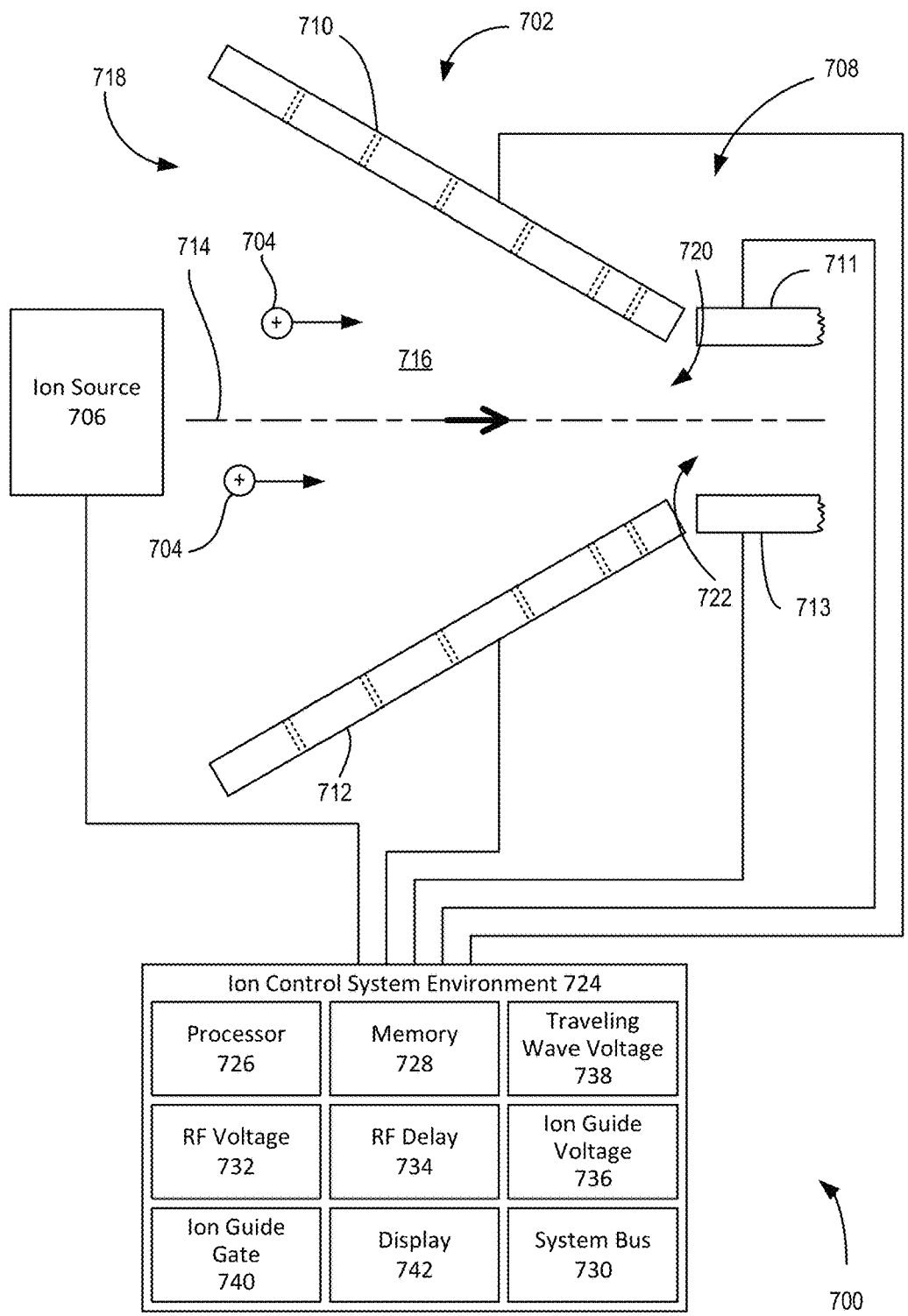
FIG. 7 is a schematic of an ion manipulation system.

FIG. 7 is a schematic of an ion collection system 700 that includes an ion focusing device 702 that is situated to collect ions 704 from an ion source 706 and to direct the ions 704 into an ion optical element 708. The ion focusing device 702 includes opposing electrode arrangements 710, 712 situated at an angle with respect to an ion optical axis 714 and each situated with a plurality of RF electrodes and traveling wave electrode sets to guide the ions 704 in an ion focus channel 716 from an input end 718 to an output end 720 to an input end 722 of the ion optical element 708. The ion optical element 708 can include opposing electrode arrangements 711, 713 that can be similar to or different from the opposing electrode arrangements 710, 712. A pair of guard electrodes (not shown) can also be situated to direct the ions 704 into the ion focus channel 716 or to prevent the ions 704 from leaving the ion focus channel 716 into or out of the plane of FIG. 7.

The ion collection system 700 also includes an ion control system environment 724 coupled to the ion focusing device 702, ion source 706, and ion optical element 708 that is operable to control ion collection and ion manipulation. The ion control system environment 724 include one or more computing devices that include at least a processor 726 and a memory 728. Computing devices can include desktop or laptop computers, mobile devices, tablets, logic controllers, etc. The processor 726 can include one or more CPUs, GPUs, ASICs, PLCs, FPGAs, PLDs, CPLDs, etc., that can perform various data processing or I/O functions associated with the ion control system environment 724. The memory 728 can be volatile or non-volatile (e.g., RAM, ROM, flash, hard drive, optical disk, etc.) and fixed or removable and is coupled to the processor 726. The memory 728 can provide storage capacity for one or more computer-readable media. One or more system buses 730 can provide a communication path between various environment components. The ion control system environment 724 can also be situated in a distributed form so that applications and tasks are performed by remote processing devices that are linked through a communications network. In a distributed computing environment, program modules and logic can be located in both local and remote memory storage devices.

The ion control system environment 724 can include RF voltage control logic 732 that controls the electric potential applied to the RF electrodes of the electrode arrangements 710, 712. An RF phase delay 734 can be used for alternate adjacent RF electrodes in the electrode arrangements 710, 712 so that a selected phase delay (e.g., 180 degrees) can be applied between adjacent RF electrodes. In some examples, the RF voltage control logic 732 can also control the electric potential applied to RF electrodes of the opposing RF electrode arrangements 711, 713 and such applied voltage can be synchronized with a zero delay or non-zero delay with selected RF electrodes of the electrode arrangements 710, 712, such as those that are longitudinally matched at the output end 722 of the ion focusing device 702 and the input end of the ion optical element 708. In further examples, the ion control system environment 724 can detect or receive an ion guide voltage 736 from the ion optical element 708 and apply an RF voltage to the RF electrodes of the electrode arrangements 710, 712 based on RF voltage characteristics (e.g., phase, frequency, amplitude) of the ion guide voltage 736. In additional examples, a traveling wave voltage control logic 738 can control traveling wave electric potentials that are applied to traveling wave electrodes of the electrode arrangements 710, 712 so as to direct the ions 704 towards the output end 720. In some embodiments, traveling wave electric potentials can also be controlled for traveling wave electrode sets of electrode arrangements 711, 713 in the ion optical element 708. In some examples, traveling wave characteristics can be synchronized between the electrode arrangements 710, 711 and electrode arrangements 712, 713 so as to form a smooth or continuous traveling wave coupling between the ion focusing device 702 and the ion optical element 708. In additional embodiments, the ion control system environment 724 can include an ion guide gate logic 740 that controls generation and/or emission of ions from the ion source 706. The ion guide gate logic 740 can also be synchronized to the traveling wave voltage control logic 738 so as to queue or position the ions 704 in the ion focusing device 702 so that groups of the ions 704 are controllably released or directed into the input end 722 of the ion optical element 708. In some examples, various voltage waveforms, ion characteristics, or other system parameters or performance outputs can be displayed on a display 742.

Figure 8:
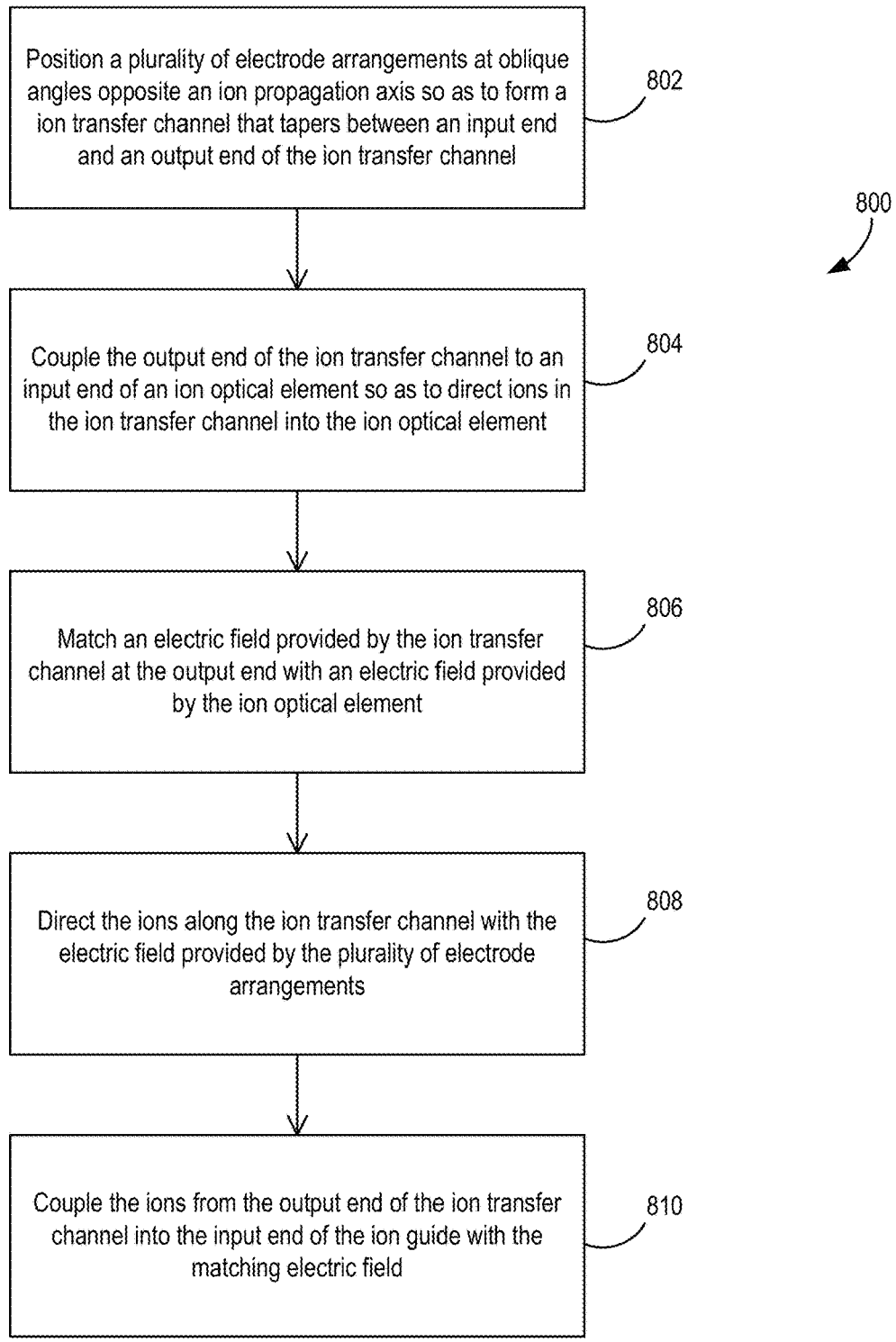
FIG. 8 is a flowchart of an example method of directing ions.

FIG. 8 shows a method 800 for directing ions. At 802, a plurality of typically planar electrode arrangements are positioned oppositely at oblique angles to an ion propagation axis so as to form a ion transfer channel that tapers between an input end and an output end of the ion transfer channel. The tapered ion transfer channel can be used to collect ions from an ion source and to transmit the ions, including losslessly in some examples, to an ion optical element. At 804, the output end of the ion transfer channel is coupled to an input end of the ion optical element so that ions in the ion transfer channel can be directed through the ion transfer channel and into the ion optical element. In representative embodiments, at 806, an electric field provided in the ion transfer channel by the electrode arrangements at the output end is matched to an electric field provided by the ion optical element at the input of the ion optical element.

Having described and illustrated the principles of the disclosed technology with reference to the illustrated embodiments, it will be recognized that the illustrated embodiments can be modified in arrangement and detail without departing from such principles. For instance, elements of the illustrated embodiments shown in software may be implemented in hardware and vice-versa. Also, the technologies from any example can be combined with the technologies described in any one or more of the other examples. It will be appreciated that procedures and functions such as those described with reference to the illustrated examples can be implemented in a single hardware or software module, or separate modules can be provided. The particular arrangements above are provided for convenient illustration, and other arrangements can be used.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope of the appended claims.

We claim:

1. An apparatus, comprising:
a plurality of electrode arrangements spaced apart from each other opposite an ion propagation axis and defining an ion transfer channel that extends along the ion propagation axis that tapers between an input end that is situated to receive ions and an output end that is situated to couple the received ions to an input end of an ion guide;
wherein the electrode arrangements are arranged in respective electrode arrangement surfaces;
wherein at least one of the electrode arrangements includes a plurality of RF electrodes extending in the direction of the ion propagation axis in the surface of the at least one electrode arrangement so that RF electrodes are situated to direct the ions away from the at least one electrode arrangement;
wherein the at least one electrode arrangement includes a plurality of traveling wave electrode sets interspersed between the RF electrodes and extending in the direction of the ion propagation axis in the surface of the at least one electrode arrangement so that the traveling wave electrode sets are situated to direct the ions towards the output end of the ion transfer channel.

2. The apparatus of claim 1, wherein the received ions are coupled at the output end to the input end of the ion guide with an electric field that is matched to the input end of the ion guide.

3. The apparatus of claim 1, wherein the respective electrode arrangement surfaces are planes, each extending at a respective oblique angle with respect to the ion propagation axis.

4. The apparatus of claim 3, wherein each of the respective oblique angles is less than or equal 60 degrees and greater than or equal 5 degrees.

5. The apparatus of claim 1, wherein the at least one electrode arrangement is tapered such that there are fewer RF electrodes and traveling wave electrode sets at the output end of the ion transfer channel than at the input end of the ion transfer channel.

6. The apparatus of claim 1, wherein at least one of the electrodes at the input end that is not at the output end is non-rectangular based on an angle defined by the tapering of the at least one electrode arrangement.

7. The apparatus of claim 1, further comprising guard electrodes situated opposite the plurality of RF electrodes and plurality of traveling wave electrode sets of the at least one electrode arrangement so as to direct the ions away from the pair of guard electrodes and into the ion transfer channel between the guard electrodes.

8. The apparatus of claim 7, wherein the guard electrodes comprise at least one or more of an opposing pair of DC electrodes, an opposing pair of RF electrode stacks, or an opposing pair of traveling wave electrode sets.

9. The apparatus of claim 1, wherein each of the traveling wave electrode sets includes a plurality of traveling wave electrodes situated to receive a traveling wave voltage that varies over time so as to direct the ions along toward the output end of the ion transfer channel.

10. The apparatus of claim 1, wherein the RF electrodes and traveling wave electrodes at the output end of the ion transfer channel are matched in at least one of size, shape, RF voltage signal, or traveling wave voltage signal of respective electrodes at the input end of the ion guide.

11. The apparatus of claim 1, wherein the ions have the same or different polarities.

12. A method, comprising:
positioning a plurality of electrode arrangements at oblique angles opposite an ion propagation axis so as to form a ion transfer channel that tapers between an input end and an output end; and
coupling the output end of the ion transfer channel to an input end of an ion optical element so as to direct ions in the ion transfer channel into the ion optical element;
wherein at least one of the electrode arrangements includes a plurality of RF electrodes and traveling wave electrode sets arranged in a surface and the arrangement is tapered in the surface such that there are fewer RF electrodes and traveling wave electrode sets at the output end of the ion transfer channel than at the input end of the ion transfer channel.

13. The method of claim 12, wherein the coupling includes matching an electric field provided by the ion transfer channel at the output end with an electric field provided by the ion optical element.

14. The method of claim 13, further comprising directing the ions at the output end into the input end of the ion optical element with the matching electric field.

15. The method of claim 12, further comprising generating ions with an ion source and collecting the ions in the ion transfer channel.

16. The method of claim 15, further comprising directing the ions in the ion transfer channel to the output end with an electric field provided by the plurality of electrode arrangements.

17. The method of claim 12, wherein the surface is a plane.

18. A method, comprising:
positioning a plurality of electrode arrangements at oblique angles opposite an ion propagation axis so as to form a ion transfer channel that tapers between an input end and an output end; and coupling the output end of the ion transfer channel to an input end of an ion optical element so as to direct ions in the ion transfer channel into the ion optical element;

wherein the electrode arrangements include guard electrodes situated opposite a plurality of RF electrodes and traveling wave electrode sets so as to direct the ions away from the pair of guard electrodes and into the ion transfer channel between the guard electrodes, and wherein the guard electrodes include at least one of an opposing pair of DC electrodes, an opposing pair of RF electrode stacks, or an opposing pair of traveling wave electrode sets.

19. A system, comprising:

at least one processor; and one or more computer-readable storage media including stored instructions that, responsive to execution by the at least one processor, cause the system to control electric potentials of RF electrodes and traveling wave electrodes in a plurality of electrode arrangements spaced apart from each other opposite an ion propagation axis and defining an ion transfer channel that extends along the ion propagation axis that tapers between an input end that is situated to receive ions and an output end that is situated to couple the received ions to an input end of an ion guide so that the ions are directed into the ion guide.

20. The system of claim 19, wherein the electrode arrangements are arranged in respective electrode arrangement surfaces.

* * * * *